United States Patent [19]

Martens et al.

[11] Patent Number: 4,470,812

[45] Date of Patent: Sep. 11, 1984

[54] CUTTING HANDPIECE AND COOLANT MEANS

[76] Inventors: Leslie V. Martens, 6956 161st La., NW., Anoka, Minn. 55303; DeWayne L. Varnes, Rte. 1, Ridgeland, Wis. 54763

[21] Appl. No.: 470,079

[22] Filed: Feb. 28, 1983

[51] Int. Cl.[3] ................................................ A61C 1/12

[52] U.S. Cl. ...................................... 433/85; 433/126; 222/386.5

[58] Field of Search ....................... 433/85, 84, 82, 80, 433/81, 83, 86, 87, 88, 104, 126; 222/386.5; 128/DIG. 12; 604/408

[56] References Cited

U.S. PATENT DOCUMENTS

| | | | |
|---|---|---|---|
| 2,459,573 | 1/1949 | Morrow | 433/84 |
| 2,884,695 | 5/1959 | Ellis | 433/82 |
| 3,079,690 | 3/1963 | Lodige | 433/81 |
| 3,505,737 | 4/1970 | Merolla | 433/82 |
| 3,640,277 | 2/1972 | Adelberg | 222/386.5 |
| 3,788,369 | 1/1974 | Killinger | 604/408 |
| 3,936,940 | 2/1976 | Loge | 433/126 |
| 3,949,753 | 4/1976 | Dockhorn | 433/84 |
| 4,075,761 | 2/1978 | Behne et al. | 433/85 |
| 4,162,030 | 7/1979 | Capra et al. | 222/386.5 |
| 4,193,197 | 3/1980 | Kuris et al. | 433/82 |

FOREIGN PATENT DOCUMENTS

| | | | |
|---|---|---|---|
| 2614776 | 12/1977 | Fed. Rep. of Germany | 433/80 |
| 561537 | 5/1975 | Switzerland | 433/84 |

*Primary Examiner*—John J. Wilson
*Attorney, Agent, or Firm*—Burd, Bartz & Gutenkauf

[57] ABSTRACT

A high-speed cutting handpiece and coolant apparatus of the type useable in dental procedures. The handpiece is of the type employing a fluid delivery conduit to provide fluid to the oral cavity of the patient for cooling and irrigating purposes. The coolant apparatus includes a cartridge having an initially empty inlet chamber and an outlet chamber initially filled with sterile solution. The chambers are separated by pressure communicative means. The cartridge is disposed in interrupting relationship to the fluid delivery conduit such that fluid from a source is introduced into the inlet chamber which displaces the sterile solution to move it through the downstream end of the fluid delivery conduit.

12 Claims, 8 Drawing Figures

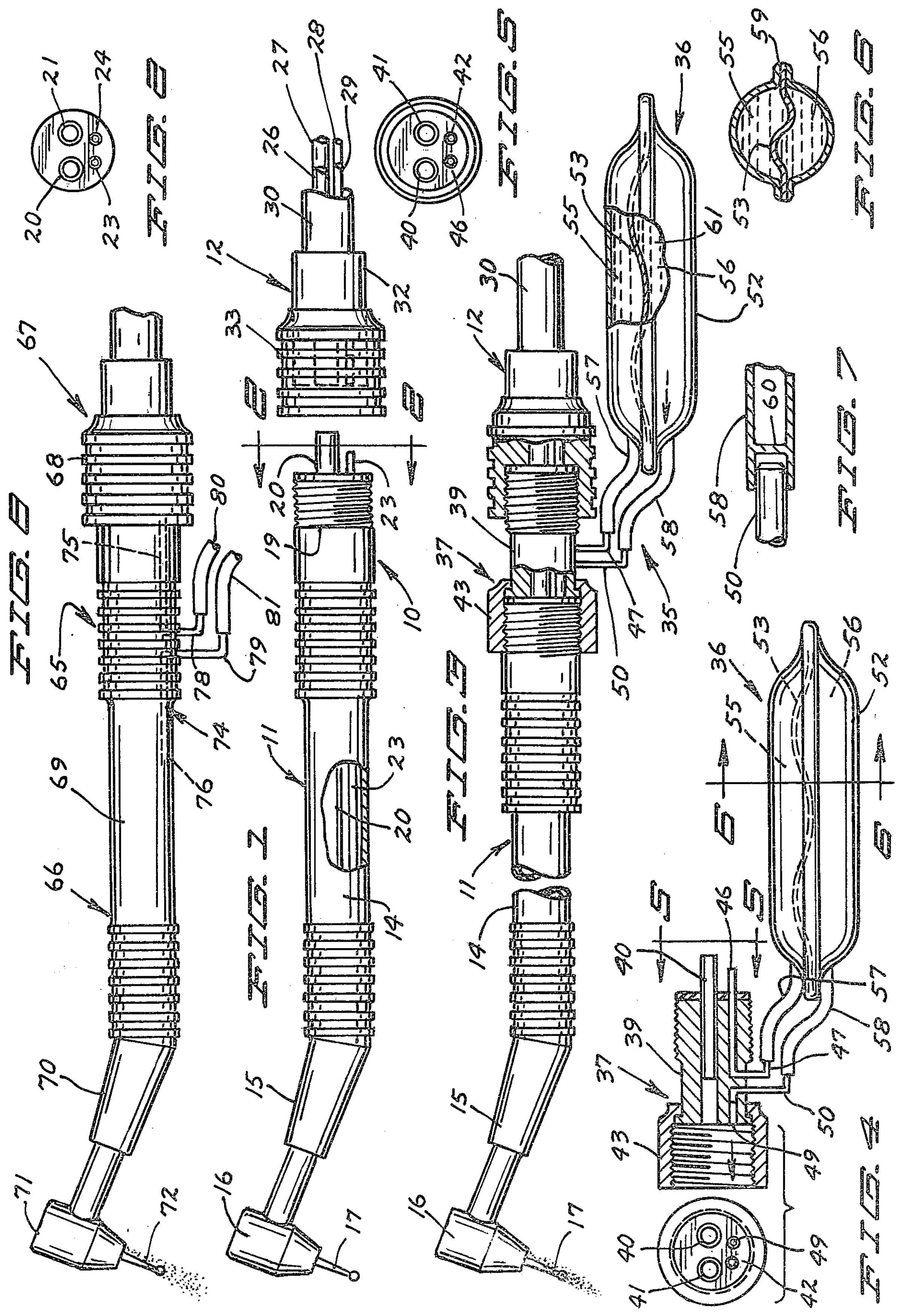

CUTTING HANDPIECE AND COOLANT MEANS

SUMMARY OF THE INVENTION

In the fields of dentistry and oral surgery, the air turbine driven, high-speed handpiece has today virtually supplanted the belt-driven ball bearing handpiece for routine intraoral use. High-speed rotary cutting devices offer a considerable time savings advantage over earlier ball bearing types; however, a coolant must be employed with these devices since considerable heat is generated through friction in the cutting of hard tissues (bone or teeth). Research indicates that liquid coolant in the form of a power mist spray is most effective in preventing thermal damage to vital oral tissues. In addition to cooling the cutting instrument, the spray also functions to irrigate the surgical site, facilitating the removal of debris generated during the cutting procedure.

Ideally, the coolant media should be sterile, isotonic and near body temperature. Currently, however, all high-speed handpieces in routine use are designed to use the community water supply for the coolant media. Not only does water quality vary from one geographic area to another, but it is also known to vary over time at the same location. Particularly, when water is heated to the ideal temperature for surgical cooling and irrigating purposes, bacterial counts may reach undesirable levels. Water samples collected at a large metropolitan dental clinic and submitted for bacteriological analysis showed, for example, that bacterial concentrations varied from 320 CFU/ml (colony forming units per milliliter) for city tap water up to 630,000 CFU/ml of tepid city water delivered through a previously sterilized handpiece.

With the recent advent of the ethylene oxide sterilizer, virtually all reuseable armamentarium placed in the oral cavity during preventive, restorative or surgical procedures can now be sterilized. Modern technology has also developed other items which, for purposes of practicality or sterility, are used only once and are then discarded. Examples include disposable injection needles, gloves, scalpel handles and blades, rinse cups, surgical masks and suturing materials.

Current technology permits the dental surgeon to operate under asceptic conditions for the most part. However, the weak link in the chain is the use of coolant media as described which is not sterile. Moreover, current routine apparatus and methods promote patient cross contamination. While the handpiece is separable from the coolant delivery tube structure for sterilization, the handpiece tubing which delivers the coolant cannot be sterilized. Since the tubing is not changed from patient to patient, cross contamination is not only possible, but probable. With conventional apparatus, upon termination of spraying of coolant media, some fluid is drawn by the apparatus from the patient back into the handpiece to eliminate objectionable dripping from the handpiece. This residual fluid can contain microorganisms which are drawn through the handpiece and migrate into the handpiece coolant delivery tubing where they may harbor, multiply and be forcibly introduced into the body tissues of subsequent patients. At best, the transmittal of microorganisms from one patient to another may (1) not produce a pathogenic infection, (2) produce a subclinical infection, or (3) produce what might be diagnosed as an idiopathic infection from which the patient recovers uneventfully. However, the transmittal of organisms associated with diseases such as oral herpes and hepatitis via the handpiece coolant is indeed of prime concern. Also of concern is the introduction of high concentrations of microorganisms into the oral cavity of medically compromises patients, especially those with respiratory disease.

The invention pertains to a high-speed rotary cutting tool of the type useable in dental and surgical procedures, and to a disposable cartridge for use therewith for providing a sterile coolant and irrigating medium isolated from, but delivered under the influence of, pressure provided by a community water supply. The cartridge comprises a flexible outer housing divided into two chambers by pressure communicating dividing means movable with respect to the housing to vary the volumes of the chambers in reciprocal fashion. The cartridge is interposed in the normal coolant delivery line of the high-speed handpiece. One of the chambers of the cartridge contains a sterile isotonic coolant solution and is connected to the coolant output line of the handpiece. The other chamber is initially empty and is connected to the normal coolant input line of the handpiece hose coupler, which is connected to the community water supply. As the coolant control is actuated in normal fashion, water from the community water supply is introduced into the inlet chamber which moves coolant solution out of the coolant chamber through the coolant delivery line of the high-speed handpiece. When the coolant chamber is depleted, the cartridge is replaced. With sterilization of the high-speed handpiece, there is no cross contamination of patients. A sterile, isotonic and tepid coolant solution can be provided. Handpiece maintenance is lowered due to the prevention of an accumulation of clogging mineral precipitates normally associated with a community water supply.

IN THE DRAWINGS

FIG. 1 is a side elevational view of a high-speed cutting handpiece in disassembled relationship to a handpiece hose supply assembly;

FIG. 2 is a sectional view of a portion of the handpiece assembly of FIG. 1 taken along the line 2—2 thereof;

FIG. 3 is a side elevational view partly in section of the handpiece assembly of FIG. 1 having coolant means according to the present invention installed thereon;

FIG. 4 is a side elevational view partly in section of the coolant means of the invention of FIG. 3;

FIG. 5 is a sectional view of a portion of the coolant means of FIG. 4 taken along the line 5–5 thereof;

FIG. 6 is a sectional view of a portion of the coolant cartridge of FIG. 4 taken along the line 6–6 thereof;

FIG. 7 is an enlarged view, partly in section, showing the tip of the fluid outlet terminal in poised relationship to the fluid outlet of the coolant cartridge; and FIG. 8 is a side elevational view, partly in section, of a cutting handpiece according to a second form of the invention.

DESCRIPTION OF A PREFERRED EMBODIMENT

Referring to the drawings, there is shown in FIG. 1 a conventional high-speed dental handpiece assembly indicated generally at 10 and comprising a handpiece 11 shown in disassembled relationship to a hose coupler assembly 12. Handpiece 11 is separable from hose coupler assembly 12 for purposes of sterilization and the like, and includes an elongate tubular body portion 14 connected to a neck 15 terminating in a head 16. Head 16 carries a cutting element shown as a drill bit 17 although other cutting elements could be employed such as a side cutting saw bit.

Drill bit 17 is driven at high speed by an air turbine motor located in head 16 (not shown). Separate discharge orifices are provided in head 16 for projecting compressed chip air to clear debris from the working site and for providing a spray of coolant at the working location of drill bit 17 to cool the drill bit and irrigate the working field. In the conventional configuration of FIG. 1, hose coupler assembly 12 connects to the upstream or inlet end of handpiece 11 to provide handpiece 11 with necessary coolant fluid and compressed air. The coolant fluid is usually water from a community supply. Handpiece 11 has an exteriorly threaded upstream end 19 and carries turbine drive air and turbine exhaust air conduits 20, 21, coolant conduit 23 and chip air conduit 24. Each conduit is tubular and extends outwardly a short distance from end 19 of handpiece 11, and then internally through handpiece 11 to head 16. Upon actuation of suitable controls, compressed air is provided through drive air conduit 20 and returns through exhaust air conduit 21 to drive the turbine and rotate the cutting piece. Upon actuation of other standard controls, coolant and chip air are provided to the working site.

Hose coupler assembly 12 connects with a turbine drive air hose 26, a turbine exhaust air hose 27, a coolant hose 28 and a chip air hose 29, all surrounded by an outer flexible tubular hose covering 30 and connected at their downstream ends to a plug-like receptacle 32. Plug 32 has suitable tubular receptacle openings connected at one end to the incoming hoses and positioned so as to properly accept the conduits of handpiece 11 in standard plug-in relationship. A collar 33 is interiorly threaded and rotatably assembled about plug 32 but longitudinally fixed thereon for connection to threaded end 19 of handpiece 11 when the conduits thereof are properly positioned in the receptacle openings of plug 32.

Referring to FIG. 3, handpiece assembly 10 includes a sterile coolant apparatus according to the invention indicated generally at 35 and including a sterile coolant cartridge 36 and a cartridge connector 37. Connector 37 is installed between handpiece 11 and hose coupler assembly 12. Connector 37 includes an insert member 39 fashioned with an upstream or inlet end corresponding to the end 19 of handpiece 11 for connection to the hose coupler assembly 12, and a downstream or outlet end corresponding to the plug end of the hose connector 12 for connection to the end 19 of handpiece 11. Insert member 39 has unimpeded conduits 40, 41 and 42 corresponding to the drive air conduit 20, exhaust air conduit 21 and chip air conduit 24 on handpiece 11 and the corresponding hoses and conduit openings on hose coupler assembly 12. On the upstream or inlet end of insert member 39, the conduits 40–42 are outwardly extended so as to engage receptacle openings of plug member 32. On the downstream end of insert member 39, the conduits 40–42 are open so as to receive in plug-like fashion the outwardly extended drive air, exhaust air and chip air conduits 20, 21 and 24. An interiorly threaded collar 43 is rotatably mounted on the downstream end of insert member 39, but longitudinally fixed thereon, and is in threaded engagement with the end 19 of handpiece 11. The opposite end of insert member 39 is exteriorly threaded for engagement with the collar 33 of hose coupler assembly 12. The conduits 40–42 provide free passage for the drive air, exhaust air and chip air.

Means are provided for the interruption of flow from coolant hose 28 and diversion to cartridge 36 for replacement by sterile coolant contained in the cartridge 36. A fourth or inlet conduit 46 extends outward from the inlet end of insert member 39 and is connectable to hose coupler assembly 12 in position to engage the receptacle opening of plug 32 connected to water hose 28 extended from the community water supply or the like. The opposite end of inlet conduit 46 extends outward of insert member 39 providing a fluid inlet terminal 47 for connection to cartridge 36. The opposite end of insert member 39 has an outlet conduit 49 with a receptacle opening in corresponding position for plug-like connection with the outwardly extended coolant conduit 23 of handpiece 11. The upstream end of conduit 49 extends outwardly of insert member 39 to provide a fluid outlet terminal 50 for connection to cartridge 36.

Cartridge 36 comprises a flexible outer housing 52 divided into two chambers by pressure communicating dividing means comprised as a diaphragm 53 movable with respect to the housing 52 to vary the volumes of the chambers in reciprocal fashion. One chamber comprises an inlet or propellent chamber 55 and the other chamber comprises an outlet or sterile media chamber 56. The diaphragm 53 divides the chambers in fluid tight relationship and is of sufficient size to be movable between opposite walls of housing 52 to virtually reduce the volume of one chamber to zero, while the other chamber occupies substantially the entire interior volume of the housing. Cartridge 36 can be composed of a disposable, flexible but inelastic plastic material and formed by a laminating process or extruding process or the like having a continuously sealed edge 59 forming the separate chambers with diaphragm 53 as shown in FIG. 6. Such a material is advantageous in terms of shipping, storage and handling and is easily disposed upon usage. Alternatively, the outer housing of cartridge 36 could be relatively rigid as of a molded plastic as might be dictated by ease of manufacturing and economy.

An inlet tube 57 communicates at one end with the interior of inlet chamber 55 and has an extendable opposite end connectable with fluid inlet terminal 47 of water delivery conduit 46. An outlet tube 58 communicates at one end with the outlet chamber 56 and has an extendable opposite end for connection to the fluid outlet terminal 50 of sterile media delivery conduit 49 for delivery of sterile media from outlet chamber 56 to the coolant conduit 23. Inlet and outlet tubes 57, 58 can be relatively short, as when cartridge 36 is small, having a relatively low volume and is held in near body portion 14. Alternatively, inlet and outlet tubes 57, 58 can be relatively elongate for locating cartridge 36 remote from body portion 14, as when cartridge 36 is larger having a relatively higher volume to provide a longer duration spray. In such case, inlet tube 57 could be connected directly to coolant supply hose near the community water source.

Initially outlet chamber 56 of cartridge 36 is filled with a sterile media indicated at 61, such as distilled water or a saline solution, with inlet chamber 55 substantially empty and having no interior volume. Cartridge 36 is fixed to connector insert member 39 as shown in FIGS. 3 and 4. The extendable end of inlet tube 57 is slip-fitted over fluid inlet terminal 47 of fluid delivery tube 46. The extendable end of outlet tube 58 is slip-fitted over the downstream end of fluid out terminal 50 of sterile media delivery conduit 49. As shown in FIG. 7, the end of outlet tube 58 can initially be sealed as by membrane 60 and can either be cut or punctured so as to be slip-fitted over terminal 50 of conduit 49. Handpiece 11 is then useable in normal fashion. Turbine input and exhaust air as well as chip air are delivered to handpiece head 16 unimpeded in the usual fashion. When the community water control is actuated, water is drawn through the coolant hose 28, through the fluid delivery conduit 46, through the inlet tube 57 to the inlet chamber 55. Under the influence of this water in inlet chamber 55, diaphragm 53 is moved and communicates the pressure to the outlet chamber 56. This moves an equal volume of sterile coolant through the outlet tube 58 and through the sterile coolant delivery conduit 23 to head 16. Only sterile coolant is discharged into the oral cavity of the patient. There is no direct communication between the community water supply and upstream portions of the water delivery tubing on the one hand and the oral cavity of the patient on the other. Upon release of the community water supply control, spray at head 16 is terminated in the usual fashion. Spray also terminates when the outlet chamber 56 of cartridge 36 is empty. The cartridge is then replaced. Between patients, handpiece 11 and connector 37 can be sterilized. A new cartridge 36 is used. There is no cross contamination between patients and only sterile fluid enters the oral cavity of each patient.

Referring to FIG. 8, there is shown a high-speed handpiece assembly according to a modified form of the invention indicated generally at 65 and having a handpiece 66 assembled to a hose coupler assembly 67 by an interiorly threaded collar 68 as previously described. Handpiece 66 has a tubular body portion 69 terminating in a neck 70 having assembled thereon a head 71. Head 71 carries a high-speed cutting element shown to comprise a drill bit 72. Handpiece 66 has air turbine drive and exhaust conduits and a chip air conduit (not shown) as previously described for coupling with appropriate supply lines carried by hose coupler assembly 67. Additionally, handpiece 66 has a coolant delivery conduit 74, which is interrupted and divided into an upstream section 75 and a downstream section 76. The downstream end of upstream section 75 terminates in a fluid inlet terminal 78 outwardly extended from body portion 69 for connection to the fluid inlet tube 80 of a disposable sterile coolant cartridge (not shown) like the coolant cartridge 36 earlier described. The upstream end of downstream section 76 terminates in a fluid outlet terminal 79 outwardly extended from body portion 69 for connection to the fluid outlet tube 81 of the sterile coolant cartridge. The upstream end of upstream section 75 of coolant conduit 74 is connected to the water line carried by hose connector assembly 67 that connects to the community water supply as earlier described.

Upon actuation of the coolant supply control, water is delivered through the upstream section 75 of coolant conduit 74 and into the inlet tube 80 to be delivered to the inlet chamber of the sterile coolant cartridge. This displaces an equal volume of sterile coolant in the outlet chamber under equal pressure causing it to flow through the outlet tube 81 and through the outlet terminal 79 of the downstream section 76 of coolant delivery conduit 74 to the head 71 where it is discharged in the usual fashion. The sterile coolant is isolated from the community water supply and only sterile coolant is delivered to the oral cavity of the patient.

While there has been shown and described certain preferred embodiments of the invention, it will be apparent to those skilled in the art that certain deviations and modifications can be had without departing from the scope and spirit of the invention.

The embodiments of the invention in which an exclusive property or privilege is claimed are defined as follows:

1. A high-speed cutting handpiece assembly of the type releasably connectable to a hose coupler assembly providing fluid and air under pressure, comprising:

an elongate tubular handpiece having a tubular body portion with a downstream discharge end carrying a power-driven, rotatable cutting element, and an upstream inlet end connectable to said house coupler assembly;

a fluid delivery conduit extended longitudinally through the tubular body portion having an inlet end connectable to a fluid delivery hose associated with the hose coupler assembly, and an outlet end for discharge of fluid proximate an intended working site of the cutting tool;

said fluid delivery conduit being interrupted in said body portion and divided into an upstream section having said inlet end and a downstream section having said outlet end, a fluid outlet terminal connected to the downstream section at the point of interruption and extended laterally outward of the body portion of the handpiece and a fluid inlet terminal connected to the upstream section at the point of interruption and extended laterally outward of the tubular body portion proximate the fluid outlet terminal;

a disposable sterile fluid cartridge comprised as a housing having an inlet chamber and an outlet chamber and including movable pressure communicating means separating the inlet chamber and the outlet chamber in fluid tight relationship and movable with respect to the housing to vary the volumes of the chambers in reciprocal fashion;

inlet means connected to the inlet chamber and releasably connected to the fluid inlet terminal adjacent the tubular body portion;

outlet means connected to the outlet chamber and releasably connected to the fluid outlet terminal adjacent the tubular body portion;

said outlet chamber of the sterile fluid cartridge filled with sterile fluid to be displaced and discharged through the discharge end of the downstream section of the fluid conduit upon selective introduction of fluid to the inlet chamber from the fluid delivery hose.

2. A high-speed cutting handpiece assembly of the type releasably connectable to a hose coupler assembly providing fluid and air under pressure, comprising:

an elongate tubular handpiece having a downstream discharge end carrying a power-driven, rotatable cutting element, and an upstream inlet end connectable to said hose coupler assembly;

a fluid delivery conduit located in the handpiece having an inlet end connectable to a fluid delivery hose associated with the hose coupler assembly, and an outlet end for discharge of fluid proximate an intended working site of the cutting tool;

said fluid delivery conduit being divided into an upstream section having said inlet end and a downstream section having said outlet end, and a fluid outlet terminal connected to the downstream section and a fluid inlet terminal connected to the upstream section, said terminals being outwardly extended from the handpiece;

said handpiece including a handpiece body portion and a connector connectable between the upstream end of the handpiece body portion and said hose coupler assembly, said connector carrying a portion of the fluid delivery conduit and having the fluid outlet terminal and the fluid inlet terminal;

a disposable sterile fluid cartridge comprised as a housing having an inlet chamber and an outlet chamber and including movable pressure communicating means separating the inlet chamber and the outlet chamber in fluid tight relationship and movable with respect to the housing to vary the volumes of the chambers in reciprocal fashion;

inlet means connected to the inlet chamber and releasably connected to the fluid inlet terminal;

outlet means connected to the outlet chamber and releasably connected to the fluid outlet terminal;

said outlet chamber of the sterile fluid cartridge adapted to initially be filled with sterile fluid to be displaced and discharged through the discharge end of the downstream section of the fluid conduit upon selective introduction of fluid to the inlet chamber from the fluid delivery hose.

3. The handpiece assembly of claim 2 wherein: power means for rotation of the cutting elements includes air turbine means, said handpiece having drive-air and exhaust-air conduits to drive the air turbine means, said connector having passages for connection of the drive-air and exhaust-air conduits of the handpiece to corresponding hoses carried by the hose coupler assembly.

4. The handpiece assembly of claim 3 wherein: the inlet means of the sterile coolant cartridge comprises an inlet tube connected at one end to the inlet chamber and connectable in slip-fit relationship to the fluid inlet terminal, said outlet means comprising an outlet tube connected at one end to the outlet chamber and connectable at the opposite end in slip-fit relationship to the fluid outlet terminal.

5. The handpiece assembly of claim 3 wherein: said sterile coolant cartridge housing is comprised of a flexible material, said dividing means being comprised of a diaphragm located within the housing dividing the housing into the inlet and outlet chambers, said diaphragm being movable sufficiently within the housing to reduce the volume of either chamber to zero.

6. The handpiece assembly of claim 5 wherein: the inlet means of the sterile coolant cartridge comprises an inlet tube connected at one end to the inlet chamber and connectable in slip-fit relationship to the fluid inlet terminal, said outlet means comprising an outlet tube connected at one end to the outlet chamber and connectable at the opposite end in slip-fit relationship to the fluid outlet terminal.

7. The handpiece assembly of claim 3 wherein: said fluid and air conduits are outwardly extended from the end of the handpiece body portion, said connector having a downstream end with plug-like receptacles for receipt of the conduits, and an upstream end having corresponding outwardly extended conduit passages for connection to a plug-like receptacle of the hose coupler assembly.

8. The handpiece assembly of claim 7 wherein: said sterile coolant cartridge housing is comprised of a flexible material, said dividing means being comprised as a diaphragm dividing the housing into said inlet and outlet chambers and movable sufficiently with respect to the housing between positions reducing the volume of either chamber to zero, said inlet means being comprised as an inlet tube connected at one end to the inlet chamber and connectable at the opposite end in slip-fit relationship to the fluid inlet terminal, said outlet means comprising an outlet tube connected at one end to the outlet chamber and connectable at the opposite end in slip-fit relationship to the fluid outlet terminal.

9. A disposable sterile fluid cartridge for use with a high-speed cutting handpiece assembly of the type having an elongate tubular handpiece with a cutting assembly at a downstream end thereof and releasably connectable at the upstream end thereof to a hose coupler assembly to provide air and fluid under pressure, and having a fluid conduit extending from the upstream end of the handpiece to the downstream end of the handpiece for discharge of fluid proximate the working site of the cutting assembly, said fluid conduit being interrupted and having an upstream section with a fluid inlet terminal outwardly extended from the handpiece, and a downstream section with a fluid outlet terminal outwardly extended from the handpiece, said cartridge comprising:

a housing having an inlet chamber and an outlet chamber and including movable pressure communicating diaphragm separating the inlet chamber and the outlet chamber in fluid tight relationship and movable with respect to the housing to vary the volumes of the chambers in reciprocal fashion;

inlet means connected to the inlet chamber and releasably connected to the fluid inlet terminal of the handpiece assembly; and outlet means connected to the outlet chamber and releasably connected to the fluid outlet terminal of the handpiece assembly, said inlet and outlet means comprising relatively short connectors which position the housing in close proximity to the handpiece assembly, said outlet chamber filled with sterile coolant fluid to be displaced and discharged through the downstream end of the downstream section of the fluid conduit upon selective introduction of fluid to the inlet chamber.

10. The sterile fluid cartridge of claim 9 wherein: said inlet means is comprised as an inlet tube connected at one end to the inlet chamber and connectable at the opposite end in slip-fit relationship to the fluid inlet terminal, said outlet means comprised as an outlet tube connected at one end to the outlet chamber and connectable at the opposite end in slip-fit relationship to the fluid outlet terminal.

11. The sterile fluid cartridge of claim 10 wherein: said housing is formed of a flexible material and said diaphragm is movable sufficiently with respect to the housing between positions reducing the volume of either chamber to zero.

12. The sterile fluid cartridge of claim 10 wherein: said outlet tube is sealed at the end connectable to the fluid outlet terminal adapted to be opened upon connection to the fluid outlet terminal, said outlet chamber being filled with a sterile coolant fluid.

* * * * *

UNITED STATES PATENT AND TRADEMARK OFFICE

CERTIFICATE OF CORRECTION

PATENT NO. : 4,470,812

DATED : September 11, 1984

INVENTOR(S) : Leslie V. Martens and DeWayne L. Varnes

It is certified that error appears in the above-identified patent and that said Letters Patent is hereby corrected as shown below:

Column 5, line 19, "house" should be -- hose --.

Signed and Sealed this

*Twenty-first* Day of *May 1985*

[SEAL]

*Attest:*

DONALD J. QUIGG

*Attesting Officer* *Acting Commissioner of Patents and Trademarks*